United States Patent
Xie et al.

(10) Patent No.: US 10,588,604 B2
(45) Date of Patent: Mar. 17, 2020

(54) AUTOCORRELATION GUIDED CROSS-CORRELATION IN ULTRASOUND SHEAR WAVE ELASTOGRAPHY

(71) Applicant: KONINKLIJKE PHILIPS N.V., Eindhoven (NL)

(72) Inventors: Hua Xie, Cambridge, MA (US); Shiwei Zhou, Yorktown Heights, NY (US); Jean-Luc Robert, Cambridge, MA (US); Vijay Thakur Shamdasani, Kenmore, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 34 days.

(21) Appl. No.: 15/311,553

(22) PCT Filed: May 11, 2015

(86) PCT No.: PCT/IB2015/053441
§ 371 (c)(1),
(2) Date: Nov. 16, 2016

(87) PCT Pub. No.: WO2015/173709
PCT Pub. Date: Nov. 19, 2015

(65) Prior Publication Data
US 2017/0079620 A1 Mar. 23, 2017

Related U.S. Application Data
(60) Provisional application No. 61/994,370, filed on May 16, 2014.

(51) Int. Cl.
*A61B 8/08* (2006.01)
*G01S 7/52* (2006.01)
*A61B 8/00* (2006.01)

(52) U.S. Cl.
CPC .......... *A61B 8/5215* (2013.01); *A61B 8/4245* (2013.01); *A61B 8/4477* (2013.01); *A61B 8/485* (2013.01); *G01S 7/52022* (2013.01)

(58) Field of Classification Search
CPC ..... A61B 8/4245; A61B 8/4477; A61B 8/485; A61B 8/521; G01S 7/52022
See application file for complete search history.

(56) References Cited

U.S. PATENT DOCUMENTS

| | | | |
|---|---|---|---|
| 7,873,686 B2 | 1/2011 | Elfataoui et al. | |
| 2012/0095333 A1* | 4/2012 | Jiang | A61B 5/0053 600/438 |

(Continued)

FOREIGN PATENT DOCUMENTS

| | | |
|---|---|---|
| AL | 2011001333 A1 | 1/2011 |
| JP | 2012081269 A | 4/2012 |

(Continued)

OTHER PUBLICATIONS

Chen et al., "Improvement of Elastographic Displacement Estimation using a Two-Step Cross-Correlation Method", Ultrasound Med Biol, Jan. 2007, vol. 33, Issue 1, pp. 48-56.*

(Continued)

*Primary Examiner* — Katherine L Fernandez
(74) *Attorney, Agent, or Firm* — Sherry Austin

(57) ABSTRACT

Ultrasound motion-estimation includes issuing multiple ultrasound pulses, spaced apart from each other in a propagation direction of a shear wave, to track axial motion caused by the wave. The wave has been induced by an axially-directed push. Based on the motion, autocorrelation is used to estimate an axial displacement. The estimate is used as a starting point (234) in a time-domain based motion tracking algorithm for modifying the estimate so as to yield a modified displacement. The modification can constitute an improvement upon the estimate. The issuing may corre- (Continued)

spondingly occur from a number of acoustic windows, multiple ultrasound imaging probes imaging respectively via the windows. The autocorrelation, and algorithm, operate specifically on the imaging acquired via the pulses used in tracking the motion caused by the wave that was induced by the push, the push being a single push. The algorithm may involve cross-correlation over a search area incrementally increased subject to an image matching criterion (S358).

23 Claims, 5 Drawing Sheets

(56) References Cited

U.S. PATENT DOCUMENTS

| | | | | |
|---|---|---|---|---|
| 2012/0116220 A1* | 5/2012 | Burcher | ............... | A61B 5/0048 600/438 |
| 2012/0158323 A1 | 6/2012 | Hazard et al. | | |
| 2013/0296698 A1* | 11/2013 | Fraser | ............... | A61B 8/4488 600/438 |

FOREIGN PATENT DOCUMENTS

| | | |
|---|---|---|
| JP | 2012531937 A | 12/2012 |
| JP | 2012533329 A | 12/2012 |
| WO | 2011007278 A2 | 1/2011 |
| WO | 2011064688 A1 | 6/2011 |
| WO | 2013147298 A1 | 10/2013 |

OTHER PUBLICATIONS

Pesavento et al., "A Time-Efficient and Accurate Strain Estimation Concept for Ultrasonic Elastography Using Iterative Phase Zero Estimation", Sep. 1999, vol. 46, No. 5, pp. 1057-1067.*

Shiina, et al., "Real-time Tissue Elasticity Imaging using the Combined Autocorrelation Method", MEDIX Suppl 2007, Jan. 1, 2007 (Abstract).

Azar et al., "Motion Estimation in Ultrasound Images Using Time Domain Cross Correlation With Prior Estimates", IEEE Transactions on Biomedical Engineering, vol. 53, No. 10, Oct. 1, 2006, pp. 1990-2000.

Chen, et al., "Assessment of Liver Viscoelasticity by Using Shear Waves Induced by Ultrasound Radiation Force", Journal of Radiology, Dec. 6, 2012 published online (Abstract).

Kasai, et al., "Real-Time Two-Dimensional Blood Flow Imaging Using an Autocorrelation Technique", IEEE Transactions on Sonics and Ultrasonics, vol. SU-32, No. 3, May 1985, pp. 458-464.

Loupas, et al., "An Axial Velocity Estimator for Ultrasound Blood Flow Imaging, Based on a Full Evaluation of the Doppler Equation by Means of Two-Dimensional Autocorrelation Approach", IEEE Trans. Ultrason. Ferroelectr. Freq. Control, vol. 42, Issue 4, 1995, pp. 672-688 (Abstract).

Lubinski, et al., Speckle Tracking Methods of Ultrasonic Elasticity Imaging Using Short-Time Correlation, IEEE Transactions on Ultrasonics, Ferroelectrics, and Frequency Control, vol. 46, No. 1, Jan. 1999, pp. 82-96.

* cited by examiner

AUTOCORRELATION GUIDED CROSS-CORRELATION IN ULTRASOUND SHEAR WAVE ELASTOGRAPHY

This application is the U.S. National Phase application under 35 U.S.C. § 371 of International Application No. PCT/IB2015/053441, filed on May 11, 2015, which claims the benefit of U.S. Provisional Application Ser. No. 61/994,370, filed May 16, 2014. These applications are hereby incorporated by reference herein.

FIELD OF THE INVENTION

The present invention relates to tracking shear-wave-induced motion and, more particularly, to the use of correlation in the motion tracking.

BACKGROUND OF THE INVENTION

Ultrasound shear wave elastography is a new medical modality that can measure mechanical properties of soft tissue such as shear modulus and shear viscosity. As tissue elasticity is related to pathology, elastography can provide additional clinical information to increase diagnostic confidence. One example is non-invasive liver fibrosis staging by measuring liver stiffness.

In acoustic-radiation-force based ultrasound shear wave elastography, the dedicated pulse sequence consists of one or more long push pulses (typically hundreds of microseconds long each) and a series of interleaved tracking pulses. Due to the effect of acoustic radiation force, the push pulse causes tissue in the focal area to move away from the probe surface, simultaneously establishing a shear wave propagating away from the focal region in a direction perpendicular to the push beam. For each lateral position along the shear wave pathway at the focal depth, the tissue motion induced by the shear wave will be mainly in the same direction as the push beam. Consequently, the tracking pulses can, for a given position, monitor such dynamic response and translate it into a position-specific displacement waveform representing the magnitude of tissue movement as a function of time. Such waveforms can be computed at multiple positions along the shear wave propagation path. The waveforms can be inputted into a process for calculating the speed of the propagation. For example, Fourier transform can be performed on those shear waveforms to estimate shear wave phase velocity. Alternatively, shear wave amplitude peak-to-peak spatial and temporal calculations can also yield the shear wave propagation speed. As a result, absolute values of tissue mechanical properties can be determined. In particular and by way of example, the speed at which a shear wave propagates inside the tissue is governed by shear modulus, shear viscosity, tissue density and shear wave frequency through some mechanical models. The stiffer the tissue is, the faster the waves move. A measure of the stiffness can then be used in, for example, liver fibrosis staging.

Accurate, reliable and efficient motion tracking is a goal in the final estimation of tissue properties in any form of ultrasound shear wave elastography. In general, there are two major motion tracking techniques in ultrasound imaging: 1) phase shift by auto-correlation, and 2) time-shift by cross-correlation (or other alternatives such as sum absolute difference (SAD)).

In autocorrelation based approaches, the displacement of the structures of interest induces phase shift on successive high frequency ultrasound echoes backscattered by the moving medium. Autocorrelation has been implemented on most commercial ultrasound systems for real-time color flow imaging. As ultrasound waves propagate through soft tissue, the spectrum experiences a downshift due to the frequency dependent attenuation. Therefore, assuming a constant center frequency in Doppler-based approaches will result in displacement estimation error. It is known to use additional autocorrelation in the fast time domain, i.e., in the axial direction of ultrasound pulses, to estimate the local center frequency and subsequently improve the displacement estimation accuracy. See T. Loupas, J. T. Powers, and R. W. Gill, "An Axial Velocity Estimator for Ultrasound Blood Flow Imaging, Based on a Full Evaluation of the Doppler Equation by Means of Two-Dimensional Autocorrelation Approach," IEEE Trans. Ultrason. Ferroelectr. Freq. Control 42.4., pp. 672-688, 1995.

Time-shift by cross-correlation estimates time delays by cross-correlating, from one pulse to another pulse using radiofrequency (RF) data or complex signals conveyed from RF data. The search area is preset large enough to avoid missing an optimal match.

SUMMARY OF THE INVENTION

What is proposed herein below addresses one or more of the above concerns.

Two standard approaches to displacement estimation are autocorrelation and cross-correlation. Autocorrelation is more computationally efficient than cross-correlation. However it is subject to aliasing—the maximum displacement limit is a quarter wavelength (for standard liver image probe with center frequency 3 MHz, the limit is approximately 120 μm).

In the conventional, i.e., unguided, cross-correlation approach, aliasing limit is eliminated. However it takes more computational time which is proportionally related to the predefined search area. Searching over a large area makes standard cross-correlation computationally expensive. However, if the search area is set too small, the true peak of the cross correlation function will be missed; if it is too large, peak hopping will occur due to noise contained in the signals. In such case, cross-correlation can produce a false correlation peak exceeding the true peak. False peaks will introduce discontinuity and error in displacement estimation. Unfortunately, in practice, the size of a search area needed would be variable. In clinical applications, ultrasound shear wave elastography induced soft tissue motion is on the order of ten-micrometer (10-μm). The upper limit is mainly constrained by a United States Food and Drug Administration (FDA) acoustic output safety limit. The induced shear wave motion is usually observed by ultrasound tracking pulses for a period of 10-20 milliseconds (ms) for one shear wave push pulse. If multiple push pulses are used, the observation can increase to 50-100 ms. Although patients are usually advised to hold breath for a few seconds during shear wave elastography, during the period of time 50-100 ms, patient motion (cardiac motion and breathing) and background motion sometimes can exceed quarter wavelength and reach one order magnitude higher than true shear wave motion to bury the true shear wave signal. In such a case, if conventional cross-correlation alone is utilized, a very large search size has to be used in order to locate the maximum correlation function. This results in longer computational time and potentially in false peak hopping. If auto-correlation alone is used, phase aliasing will likely occur.

The two-step motion-tracking approach proposed herein is more robust to background motion.

This new approach uses both auto-correlation, and cross-correlation, for accurate and efficient tracking of shear wave propagation in soft tissue. This is useful, for example, for in vivo applications of ultrasound shear wave elastography. The two-step approach is characterizable as autocorrelation guided cross-correlation. In the first step, phase is derived from autocorrelation of the complex signals and properly un-wrapped. Initial displacement is then calculated from the phase using a constant center frequency. In the second step, the initial displacement is quantized and used as a starting point to feed the cross-correlation with a reduced search window to obtain the final displacement with high precision. By integrating autocorrelation and cross-correlation, the proposed method is well suited for real-time applications. Computation by cross-correlation in the instant proposal is much faster than standard cross-correlation. It also reduces the variance of the displacement estimates and bias, without the need for explicit estimation of the mean frequency of the RF signals.

Performance improvement of this new method over traditional autocorrelation includes that: 1) aliasing is removed; and 2) there is no need to consider effects of center frequency depth attenuation and frequency random fluctuation. The latter benefit exists because displacement estimation using time-shift based cross-correlation is immune to frequency change. Moreover, the performance improvement of this new method over traditional cross-correlation includes: 1) significantly reduced search size to overcome peak hopping (false maxima or minima) leading to improved estimation accuracy; and 2) much faster computation.

What is proposed herein combines auto-correlation and cross-correlation estimators in a way that takes advantages of the strength of each to improve overall motion tracking performance. For example, error due to any aliasing not removed by the phase unwrapping in step one is corrected or mitigated by the ensuing cross-correlation. The relatively high computational burdened of the cross-correlation, as another example, is relieved by providing the cross-correlation with a search significantly shortened by the autocorrelation-derived starting point. This composite protocol can obtain more accurate and robust displacement estimation for shear wave elastography than either individual protocol.

In accordance with an aspect of the proposed technology, an ultrasound motion-estimation method includes issuing multiple ultrasound pulses, spaced apart from each other in a propagation direction of a shear wave, to track axial motion caused by the shear wave. The shear wave has been induced by an axially-directed ultrasound, or mechanically-induced, push pulse. Based on the tracking pulse echoes, the method uses autocorrelation to estimate an axial displacement. The method then uses the estimate as a starting point in a time-domain based motion tracking algorithm for modifying the estimate so as to yield a modified displacement. The modification can constitute an improvement upon the estimate in terms of motion tracking accuracy. The issuing may correspondingly occur from a number of acoustic windows, multiple ultrasound imaging probes imaging respectively via the windows. The autocorrelation, and algorithm, can operate specifically on the imaging acquired via the pulses used in tracking the motion caused by the wave that was induced by the push, the push being a single push. The algorithm may involve cross-correlation over a search area incrementally increased subject to an image matching criterion. The acquisition for the procedure can be extended over multiple pushes.

Details of the novel, autocorrelation guided time-domain based motion tracking in shear wave elastography are set forth further below, with the aid of the following drawings, which are not drawn to scale.

DETAILED DESCRIPTION OF EMBODIMENTS

Figure 1A:
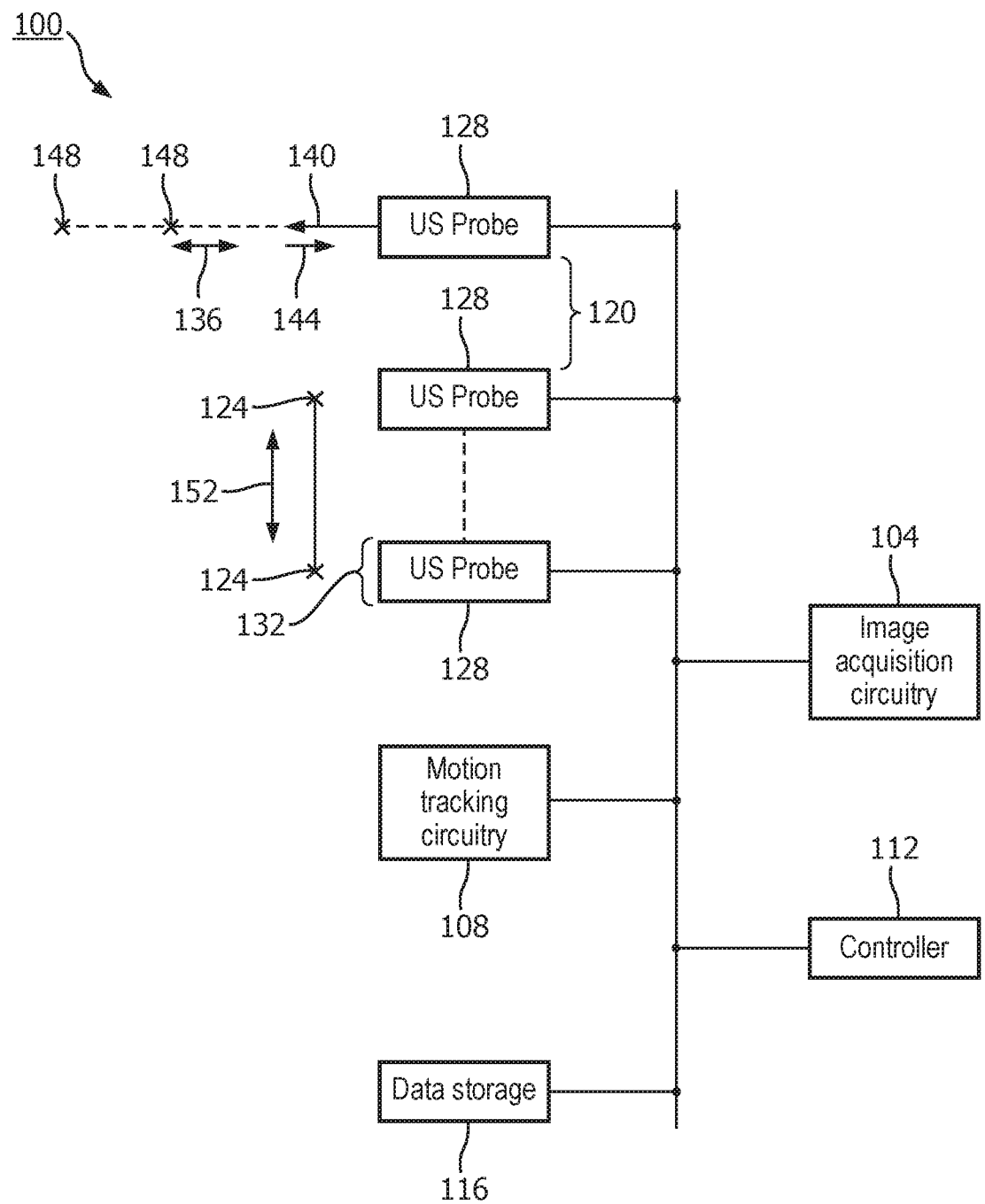
FIG. 1A is a schematic diagram of an exemplary ultrasound motion-estimation device in accordance with the present invention.

FIG. 1A depicts, by illustrative and non-limitative example, an ultrasound motion-estimation device 100 usable for shear wave elastography in autocorrelation guided time-domain based motion tracking. The device 100 includes image acquisition circuitry 104, motion tracking circuitry 108, a controller 112, and data storage 116. The image acquisition circuitry is configured for spaced apart 120 image acquisition from respective lateral positions 124. The device 100 further includes multiple ultrasound imaging probes 128. The image acquisition is performed from respective acoustic windows 132. An acoustic window is the area on the imaging surface of the probe 128 that, in contact with the object or patient (human or animal) being examined, exchanges ultrasound used in imaging. In an axial direction 136, ultrasound pulses 140 are emitted, and radiofrequency (RF) data 144 is echoed back from the patient. The pulse 140 is dynamically echoed back from a number of imaging depths 148 being sampled to interrogate the medium within the patient.

While different markings in FIG. 1A annotate different probes 128, this is for explanatory purposes. The probes 128 may be operated generally identically in imaging the medium. They may be operated simultaneously, in parallel, although what is proposed herein is not limited to such operation.

Figure 1B:
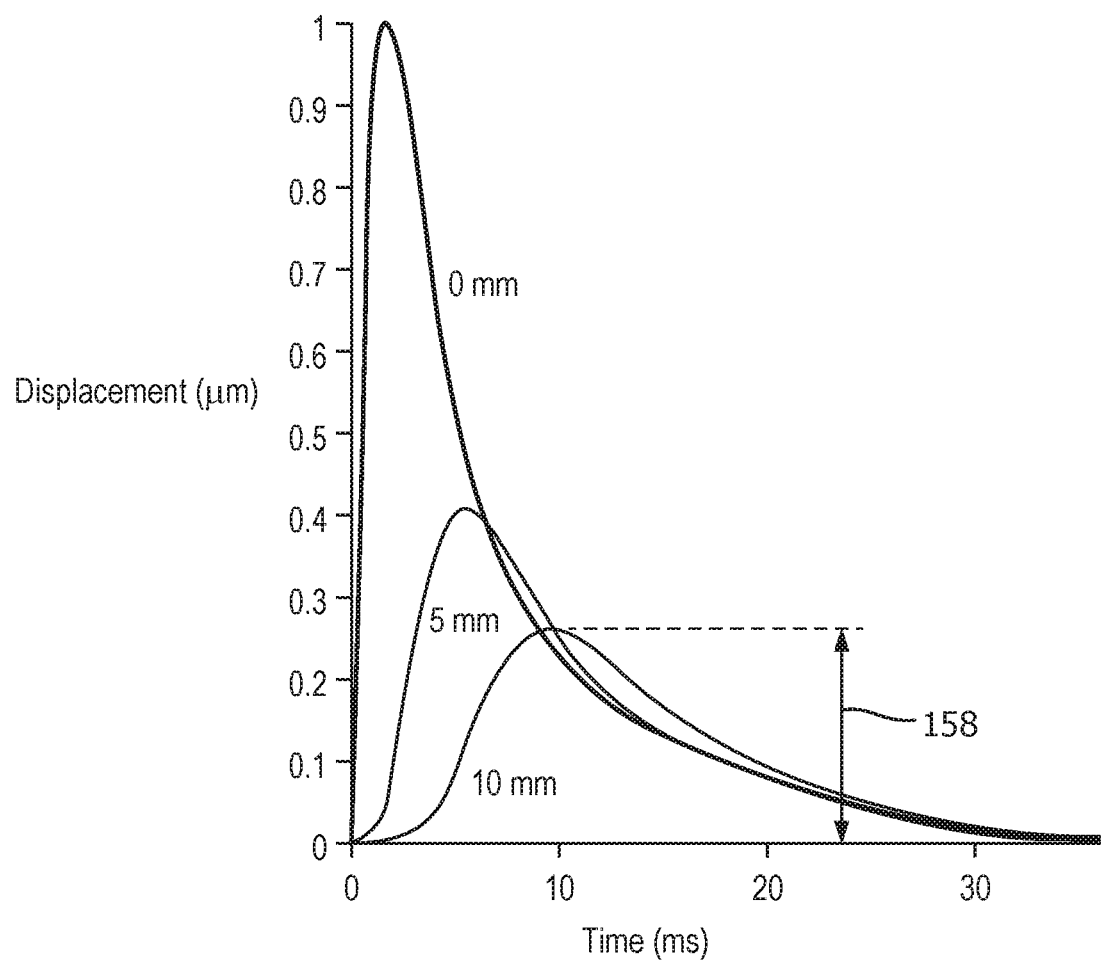
FIG. 1B is a conceptual depiction of a noise free shear wave in accordance with the present invention.

A lateral direction 152 is a direction of propagation of a shear wave that was generated by an axially-directed push. The push was generated by ultrasound focused to a particular imaging depth to deliver sufficient acoustic radiation force, or may be a mechanically induced push. It is mainly in the axial direction 136, at that imaging depth, that the propagating shear wave deforms and displaces the medium. A plot in FIG. 1B shows three waveforms representing displacement of body tissue by a shear wave. The three waveforms correspond to lateral distances of 0 mm, 5 mm and 10 mm away from the focus of the push pulse. The push pulse lasts for a few hundred microseconds, starting at the time corresponding to the origin of the plots. The tissue displacements are tracked for 35 ms. They are normalized to the peak displacement at 0 mm, for illustration purposes. The shear wave induced displacements or deformations 158 at the different lateral distances (i.e., 0 mm, 5 mm, 10 mm) manifest the displacing effect of the propagating shear wave. Their waveforms vary as a function of tissue mechanical properties and the lateral propagation distance from the shear wave origin (i.e., push pulse focus location).

Autocorrelation is, as mentioned herein above, the first step in the two-step approach to tracking axial displacement.

The displacement of structures of interest in the moving medium induces phase shift on successive high frequency ultrasound echoes backscattered by the moving medium.

The phase shift is estimated by 1-D autocorrelation of the complex signals (complex analytic or baseband signals) in the slow time. Baseband data consists of in-phase (I) and quadrature (Q) component derivable post-receive-beamforming by demodulating to remove the carrier frequency. The derivation of complex analytic signals from RF data is also well-known, and described in U.S. Pat. No. 7,873,686 to Elfataoui et al.

In shear wave tracking, $G_0(x,y)$ is the complex image acquired as the reference signal before the excitation of the push pulse. The reference pulses by which the reference image $G_0(x,y)$ was acquired are an initial part of the motion tracking. The axial direction 136 is along the x-axis, and the lateral direction 152 is along the y-axis. Each point, or "pixel", $(x_p, y_q)$ represents an image sample at an imaging depth 148 corresponding to $x_p$ and at a lateral position 124 corresponding to $y_q$;

$G_n(x,y)$ is the $n^{th}$ image acquisition, post-push, during shear wave tracking. The image acquisitions can be repeated, e.g., in parallel via the probes 128, with n ranging up to, for example, N=30 or more following a single push (N is determined by the tracking pulse repetition frequency and the tracking duration). Although, it is within the intended scope of what is proposed herein that tracking may extend past a second or even subsequent push.

Figure 2:
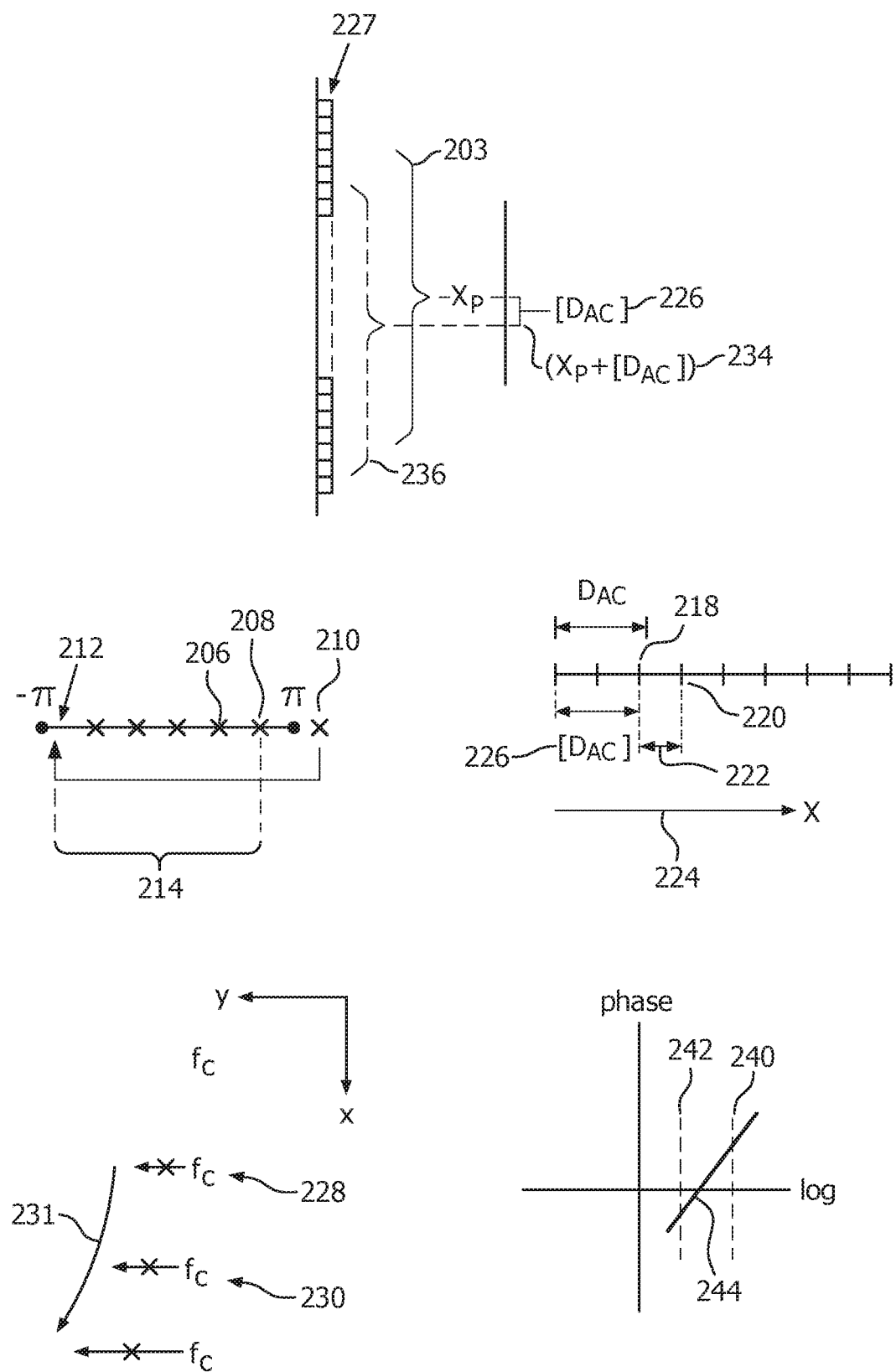
FIG. 2 is a conceptual diagram providing examples of concepts relating to operation of the device of FIG. 1A.

The generalized formula to calculate 1-D correlation $R_{k,n}$ at pixel (x,y) is expressed as below for a complex baseband signal or a complex analytic signal $$R_{k,n}(x, y) = \frac{1}{2M+1} \sum_{i=-M}^{M} Gg_0(x+i, y)G_n^*(x+i+k, y) \quad (1)$$

where (2M+1) is the size, in the axial direction 136, of the correlation kernel 203 as seen in FIG. 2; and $R_{k,n}$ is the correlation coefficient at k-lag in fast time (axial direction) and n-lag in the slow time (tracking time). $G_n^*$ is the complex conjugate of $G_n$.

The displacement D at (x,y) for the $n^{th}$ shear wave tracking acquisition is initially computed to be $$D_n(x, y) = \frac{c}{4\pi}\left(\frac{\angle R_{0,n}(x, y)}{f_c}\right), \quad (2)$$

where c is the speed of sound, $\angle R_{0,n}(x,y)$ is the angle of the 1-D autocorrelation coefficient at zero-lag in fast time and n-lag in the slow time, and $f_c$ is the center frequency. Thus, $D_n(x_p,y_q)$, after quantization which is discussed below, serves as an estimate of axial displacement of the medium, the estimate being specific for the current pixel $(x_p, y_q)$. The angle, or "phase", is derivable from the formula $$\angle R_n(x,y)=\tan^{-1}(Im[R_n(x,y)]/Re[R_n(x,y)]) \quad (3)$$

and, before substitution into equation (2), subjected to phase unwrapping to mitigate or avoid aliasing. The functions Re and Im respectively extract the real and imaginary components of the complex-valued autocorrelation coefficient $R_n$. With regard to phase unwrapping, the unwrapped phase shift in slow time (i.e., between n and n+1, where n=1, ..., N-1) is expected to be smooth without disruption. Referring to FIG. 2, a wrapped phase 206 for acquistion n is followed by a wrapped phase 208 of acquisition n+1. A phase 210 for acquisition n+2 wraps back, modulo $2\pi$, within the confining interval $[\pi,-\pi]$. This results in a wrapped phase 212, and a phase discontinuity 214 close to $2\pi$ (in magnitude and unrepresentative of the actual axial motion in the medium. Phase unwrapping resolves this, yielding the unwrapped phase 210. If, despite the phase unwrapping, disruption occurs, it usually indicates significant externally-caused motion, i.e., originating from out of the plane of the shear wave.

Equation (1) has 2M+1 sampling depths used in the kernel of auto-correlation for a specific value of "x". For any given acquisition n, samples are acquired from each of the 2M+1 sampling depths, and additional sampling depths. The additional sampling depths allow equation (1) to be executed multiples times, each time for a different value of "x." For example, in one execution, $D_n(x_p,y_q)$ is to be determined for a pixel $(x_p, y_q)$; in the next execution, $D_n(x_{p-1}, y_q)$ is to be determined for a pixel $(x_{p+1}, y_q)$, with $x_p$ and $x_{p+1}$ being at correspondingly different sampling depths.

Equation (1) is not only executed repeatedly, each time for a given pixel whose displacement estimate is being calculated; this set of executions is repeated, each time for a different acquisition n ($1 \leq n \leq N$).

Furthermore, all of the above-described executions of equation (1) are repeated each time for a different lateral position. Each lateral position 124 corresponds to a value of "y." Thus, $y_q$ has a lateral position 124 different than that of $y_{q+1}$.

In FIG. 2, two consecutive ones of the sampling depths, at a given lateral position 124, are denoted 218, 220.

In a given acquisition n at a given lateral position 124, data is acquired sampling depth 218 by sampling depth 220 for all sampling depths, during the receive window. This is all redone acquisition by acquisition. In turn, the repeated acquisitions (i.e., each being sampling depth 218 by sampling depth 220) are all redone lateral position by lateral position.

The entire set of acquisitions is done once and recorded in data storage 116, that data then being drawn on repeatedly in steps one and two.

The axial displacement D, (or "$D_{AC}$") in equation (2) is indicative of a starting point for the second step in the two-step approach.

$D_{AC}$ in equation (2), as an axial offset from the current pixel $(x_p, y_q)$, will generally have an endpoint disposed in between sampling locations.

Instead of using $D_{AC}$ itself as the starting point, $D_{AC}$ is quantized based on consecutive sampling depths 218, 220 separated by a pixel spacing unit 222 in the axial direction shown in FIG. 2 by the arrow 224. The same pixel spacing or further refined spacing (by upsampling the RF or complex signal) could be used in the second step. In the latter case, $D_{AC}$ should be adjusted using the ratio of the pixel spacing before and after upsampling.

The quantization, which may be up or down, and by rounding based on proximity or by default, results in a quantized displacement $[D_{AC}]$ 226.

This serves as the pixel-specific, i.e., specific to $(x_p, y_q)$, estimate of axial displacement of body tissue.

The pixel $(x_p, y_q)$, offset by $[D_{AC}]$, is the starting point for step two. It is this second step that fine tunes the estimate 226 from the first step—this is done via image to image matching, followed by peak searching, and polynomial fitting or image zero crossing detection, for the fine tuning.

Since the image to image matching in step two is time-domain based, there is no need for taking into account, in step one, center frequency attenuation of ultrasound issued for the acquisitions, and there is no need in step one to correct the estimate 226 for center frequency attenuation. Advantageously, center frequency attenuation correction overhead is avoided. The attenuation accumulates 231 sampling depth 228 to sampling depth 230. The "x's" crossing arrows in FIG. 2 represent the lack of need for accounting for center frequency attenuation that occurs during propagation of the tracking pulse 140.

For a cross-correlation which is part of the time-domain based motion tracking algorithm, the starting point 234 is provided as an offset 226 from the axial position, denoted "$x_p$" in FIG. 2, of the currently considered pixel ($x_p$, $y_q$). The offset, or "positioning", 226 corresponds to a shift, with respect to a reference image 227, of the correlation kernel 203 that was utilized in the autocorrelation. The shifted kernel 236 is used in the cross-correlation.

Time domain based cross-correlation estimates time delays by cross-correlating received RF echoes (or complex analytic or baseband signals) from one pulse to another pulse.

A two-dimensional cross-correlation is described immediately herein below, because steps one and two may be used to determine a two-dimensional offset. This would be for greater accuracy, in tradeoff for extra computation.

In two-dimensional ultrasound imaging, two components of a displacement vector (u,v) can be estimated using the 2-D speckle tracking procedure. Thus, "u" is in the axial direction 136 and "v" is in the lateral direction 152. In particular, at every pixel (x,y) in the initial phase-sensitive signals or images that make up the reference image $G_0$(x,y) (i.e., RF signal, complex baseband or complex analytic signal), a 2-D correlation kernel of spatial extent equaling approximately one speckle is defined around the pixel. A speckle, corresponding in size to M and J in formula (4) below, is defined as the full-width at half maximum in both dimensions of the two-dimensional autocorrelation function of the initial complex image $G_0$(x,y). This kernel is then cross-correlated with the complex image $G_n$(x,y) following deformation, i.e., post-push. The resultant 2-D weighted cross-correlation coefficient $\rho'_{k,l}$ at pixel (x,y) at $n^{th}$ acquisition as a function of 2-D lags (k,l) is calculated:

$$\rho'_{k,l,n}(x,y) = \frac{\sum_{i=-M}^{i=M}\sum_{j=-J}^{j=J} W_{ij}[G_0(x+i, y+j)G_n^*(x+k+i, y+l+j)]}{\left[\sum_{i=-M}^{i=M}\sum_{j=-J}^{j=J} W_{ij}|G_0(x+i, y+j)|^2\right]^{1/2} \left[\sum_{i=-M}^{i=M}\sum_{j=-J}^{j=J} W_{ij}|G_n(x+k+i, y+l+j)|^2\right]^{1/2}} \quad (4)$$

In this expression, $W_{ij}$ is a simple two-dimensional weighting function over the (2M+1)×(2J+1) point correlation kernel. The weighting, by weights of a weighted average, reduces the likelihood of peak hopping, and overall error, in the search for the optimal (or "maximum") lag. High frequency noise can be reduced by use of a weighting function that smoothly decreases to zero at the tails, such as a Hanning window.

The correlation coefficient is a unit-normalized, complex function of lags (k,l) with a range of ±K and ±L.

When, as in equations (1) through (3), only 1-D correlation and 1-D searching are used for tracking the axial motion, the above formula is simplified to L=0 and J=0 thereby reducing to:

$$\rho'_{k,n}(x,y) = \frac{\sum_{i=-M}^{i=M} W_i[G_0(x+i, y)G_n^*(x+k+i, y)]}{\left[\sum_{i=-M}^{i=M} W_i|G_0(x+i, y)|^2\right]^{1/2} \left[\sum_{i=-M}^{i=M} W_i|G_n(x+k+i, y)|^2\right]^{1/2}} \quad (5)$$

The corresponding correlation kernel 236 is of size 2M+1. The value "x" on the right side of equation (5) is replaced by the starting point 234, i.e., ($x_p$+[$D_{AC}$], $y_q$) for $G_n$(x,y) (0<n<=N). The lag k, and thus the range [−K,K], is incremented over iterative executions of equation (5). Thus, the extent of the search area is M+k pixel spacing units 222 on either axial side of the center of the correlation kernel 236. The lag k associated with what turns out to be the maximum value of the correlation coefficient $\rho'_{k,n}$(x,y) is used in an interpolation to find a peak of a correlation coefficient curve and the corresponding, or "maximum", lag $k_{maxI}$. Since lag $k_{maxI}$ is in the axial direction 136, it is a vector. The estimate [$D_{AC}$] 226 from step one is likewise a vector in the same direction 136. The two vectors (or equivalently scalars in the 1-D case) are added to derive a modified displacement, i.e., an improved measurement of the displacement, for pixel ($x_p$, $y_q$). In the 2-D case, both of the vectors added are two-dimensional. As an alternative to using the starting point 234 as a replacement for the value of "x" for $G_n$(x,y) (0<n<=N), ($x_p$-[$D_{AC}$], $y_q$) may be used as a replacement for "x" in $G_0$(x,y).

Figure 3A:
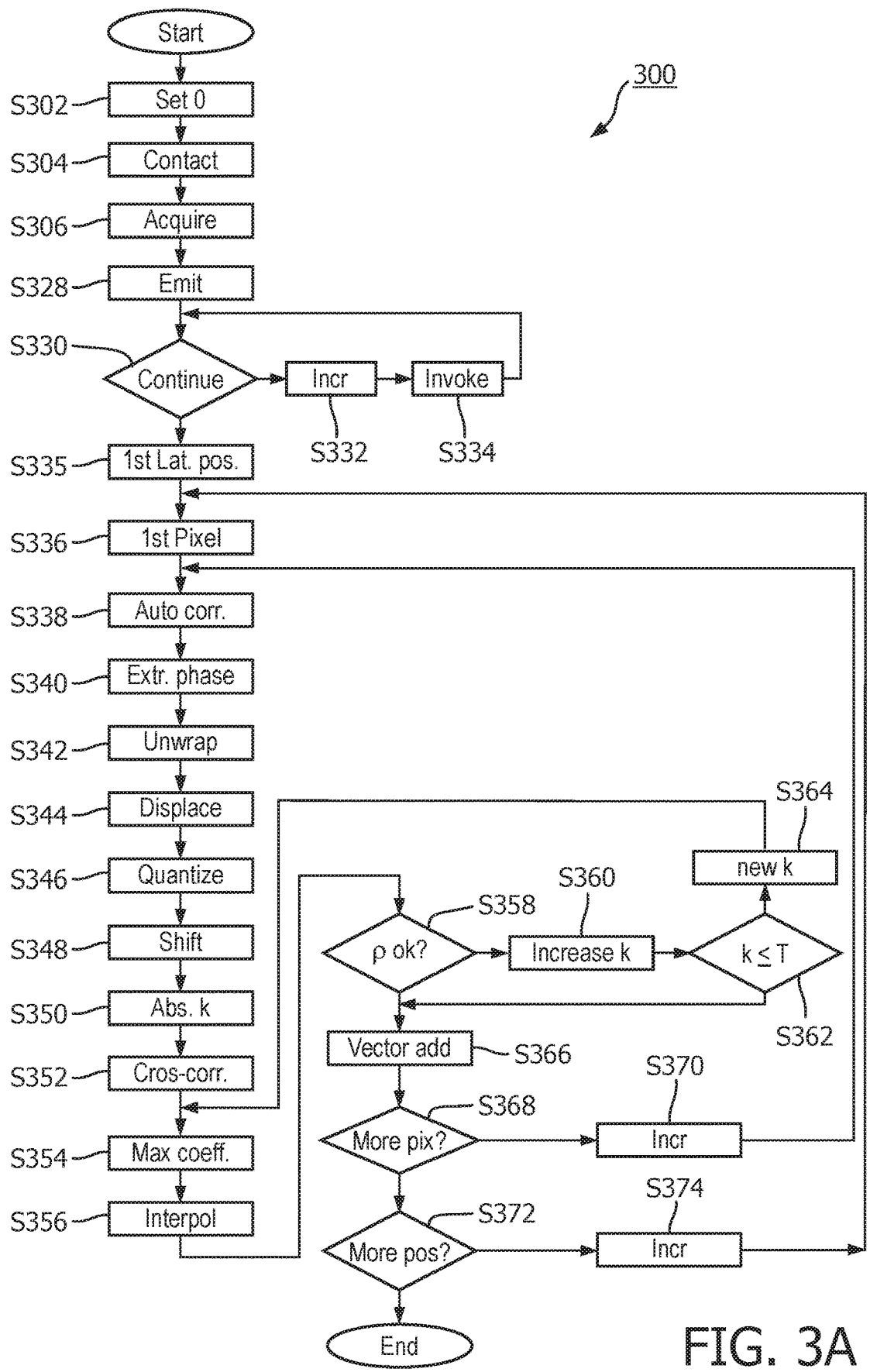
FIGS. 3A and 3B are is a set of flow charts demonstrating a possible operation for autocorrelation guided time-domain based motion tracking in shear wave elastography, according to the present invention.

Operationally and with reference to the exemplary procedure 300 in FIG. 3A, an acquisition counter is initialized to zero (step S302).

The probes 128 are positioned spaced apart 120 and in contact with the patient or subject (step S304).

The reference image 227 is acquired, i.e., an imaging acquisition is made (step S306).

Figure 3B:
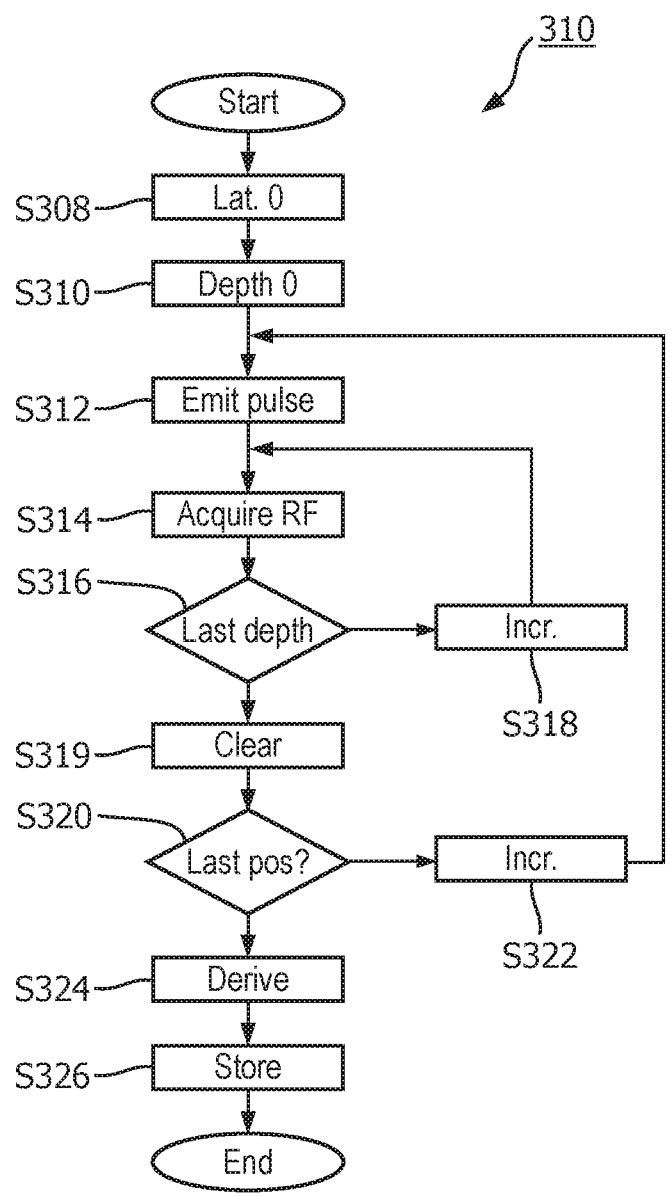

In particular, in executing step S306, an image-acquiring sub-procedure 310 (example being depicted in FIG. 3B) is invoked, and is executed as follows. A lateral position counter is initialized to zero (step S308). An imaging depth counter is likewise initialized to zero (step S310). An ultrasound pulse 140 is emitted by the probe 128 in the current lateral position 124 (step S312). An RF signal 144 is acquired from an ultrasound echo originating from the current imaging depth 148 (step S314). If it is not the last depth (step S316), the depth counter is incremented (step S318) and return in made to the sample receive step S314. If, instead, it is the last depth (step S316), the depth counter is cleared (step S319). If the current position 124 is not the last position (step S320), the position counter is incremented (step S322) and processing branches back to the pulse emitting step S312. If, on the other hand, the current position is the last position (step S320), complex analytic signals are derived from the RF data acquired (step S324). The derived analytic signals are stored in correspondence with the stored RF signals (step S326). Alternatively, complex analytic data may not be generated or needed if, for example, correlation lag interpolation is done via a polynomial fitting technique. Likewise, complex baseband data may serve the role of RF data in steps one and two.

With reference again to the main procedure 300, the push pulse is emitted (step S328). Here, it is assumed that a single push pulse is emitted for the entire procedure 300, although there alternatively could be, later on, an additional one or more push pulses to allow for extra tracking at the possible expense of more global background noise from patient motion during the time period needed for the extra tracking. If, currently, image acquisition is still to continue (step S330), the acquisition counter is incremented (step S332), the image acquisition sub-procedure 310 is invoked for tracking (step S334), and return is made to step S330. If, however, image acquisition is no longer to continue (step S330), processing points to the first lateral position 124 in the acquired data for which displacement is to be measured (step S335). Processing points to the first pixel $(x_p, y_q)$ at the current lateral position 124 (step S336). Autocorrelation according to equation (1) is performed at zero lag (step S338). Equation (3) is used to extract the phase of the complex-valued autocorrelation coefficient $R_n$ (step S340). The phase is unwrapped based on the phase determination of the prior acquisition (step S342). Equation (2) is used to estimate the axial displacement $D_{AC}$ for the current pixel (step S344). $D_{AC}$ is quantized to yield the quantized displacement $[D_{AC}]$ 226 (step S346). The correlation kernel 203 used in the autocorrelation is now shifted, resulting in a shifted kernel 236 for subsequent cross-correlation (step S348). The absolute value of a correlation lag k is initialized, based, for example, on what is expected to be the smallest search needed to correct the estimate 226 from step one (step S350). For example, a typical 100 µm predefined cross-correlation search area can be reduced to 30 µm, which is a benefit of the proposed two-step method. Cross-correlation in accordance with equation (5) draws on complex analytic signals, iteration by iteration as the lag k varies between—K and K (step S352). This is not a limitation on step one any combination of RF, complex analytic or complex baseband signals may have been used. From the set of coefficients $\rho'_{k,n}(x,y)$ generated in the iterations, a maximum coefficient $\rho_{max}$ is selected, and its phase 240 is determined, as was done for the autocorrelation coefficient (step S354). The iterative-wise closest neighboring coefficient with a phase 242 of opposite polarity is selected, and interpolation is used to determine, from a zero crossing 244, an interpolated correlation $lag_{maxI}$ and the corresponding interpolated maximum cross-correlation coefficient $\rho_{maxI}$ (step S356). If $\rho_{maxI}$ does not meet an image-matching threshold, or "criterion", $T_{IM}$ (step S358), the lag k is increased (step S360). Query is made as to whether the lag k now is greater than a maximum lag threshold $T_{ML}$ (step S362). If the lag k is not greater than $T_{ML}$ (step S362), the cross-correlation of equation (5) is repeated for each of the intervening values of k introduced by the just-previous instance of step S360 (step S364). Return is then made to step S354. If, on the other hand, $\rho_{maxI}$ does meet $T_{IM}$ (step S358) or the lag k exceeds $T_{ML}$ (step S362), a vector addition is performed, summing the quantized displacement $[D_{AC}]$ 226 with the interpolated correlation $lag_{maxI}$ (step S366). If more pixels $(x_p, y_q)$ remain to be processed (step S368), the pixel pointer is incremented (step S370) and return is made to the autocorrelation step S338. Otherwise, if no more pixels remain to be processed (step S368), but more spatial positions are to be processed (step S372), the position pointer is incremented (step S374) and processing returns to step S336.

The method proposed herein above has been validated using in vivo clinical data. Improved motion tracking success was found for the two-step method, in the post-processing of data, in comparison to other algorithms. Higher motion tracking success rate means more valid clinical data for better diagnostic performance under the same examination time.

Although methodology of the present invention can advantageously be applied in providing medical diagnosis for a human or animal subject, the scope of the present invention is not so limited. More broadly, techniques disclosed herein are directed to improved shear-wave-based motion tracking, in vivo or ex vivo.

While the invention has been illustrated and described in detail in the drawings and foregoing description, such illustration and description are to be considered illustrative or exemplary and not restrictive; the invention is not limited to the disclosed embodiments.

For example, an example of an alternative time-domain based motion tracking algorithm is the block-matching minimum difference method.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A single processor or other unit may fulfill the functions of several items recited in the claims. The mere fact that certain measures are recited in mutually different dependent claims does not indicate that a combination of these measures cannot be used to advantage.

What is claimed is:

1. An ultrasound motion-estimation device comprising:
image acquisition circuitry configured to issue, via multiple acoustic windows spaced laterally apart in a propagation direction of a shear wave, a respective plurality of ultrasound pulses to track axial motion caused by said shear wave, said shear wave having been induced by an axially-directed push, and to acquire a signal resulting from the respective plurality of ultrasound pulses, wherein the signal is based, at least in part on the axial motion, wherein the image acquisition circuitry is further configured to issue a first respective plurality of ultrasound pulses to acquire a reference signal prior to the axially-directed push; and
motion tracking circuitry configured to:
apply a one dimensional autocorrelation algorithm with a correlation kernel to the signal and the reference signal to calculate an autocorrelation coefficient;
compute an estimate of axial displacement based, at least in part, on a phase derived from the autocorrelation coefficient to produce a quantized displacement;
shift the correlation kernel by the quantized displacement to derive a shifted kernel;
apply a cross-correlation algorithm based, at least in part, on the shifted kernel to the signal and the reference signal to calculate a plurality of cross-correlation coefficients for a corresponding plurality of axial lags;
use an axial lag of the plurality of axial lags associated with a maximum cross-correlation coefficient of the plurality of cross-correlation coefficients in an interpolation to find a peak cross-correlation coefficient to derive a maximum axial lag; and sum the maximum axial lag and the quantized displacement to derive a modified measurement of the axial displacement.

2. The device of claim 1, wherein the one dimensional autocorrelation algorithm acquires samples from a number of sampling depths, wherein the number of sampling depths corresponds to a size of the correlation kernel.

3. The device of claim 2, wherein the one dimensional autocorrelation algorithm is executed multiple times, each time for a different sampling depth.

4. The device of claim 2, wherein the one dimensional autocorrelation algorithm is executed multiple times, each time for a different lateral location.

5. The device of claim 1, wherein the one dimensional autocorrelation algorithm is applied in a slow time dimension corresponding to a tracking time.

6. The device of claim 1, wherein the respective plurality of ultrasound pulses to track axial motion caused by said shear wave comprise a plurality of acquisitions and the one dimensional autocorrelation algorithm is executed for each of the plurality of acquisitions.

7. The device of claim 1, wherein the reference image comprises pixels, wherein the motion tracking circuitry is configured to repeat the autocorrelation for different ones of said pixels to position respective kernels for cross-correlation.

8. The device of claim 1, wherein the motion tracking circuitry is configured to operate, with respect to performance of said autocorrelation and of said algorithm, specifically on imaging acquired via said pulses used in tracking said motion caused by said wave that was induced by said push, said push being a single push.

9. The device of claim 1, wherein the signal is a complex signal derived from radiofrequency data.

10. The device of claim 9, wherein the signal and the reference signal include in-phase and quadrature components.

11. The device of claim 10, wherein the in-phase and quadrature components are derived by demodulating to remove a carrier frequency.

12. The device of claim 9, wherein the complex signal and the reference signal are upsampled prior to quantizing the estimated displacement.

13. The device of claim 1, wherein the motion tracking circuitry is further configured to estimate the axial displacement without taking into account center frequency attenuation of ultrasound issued in said issuing.

14. The device of claim 1, wherein the estimated displacement is adjusted based on a ratio of pixel spacing before and after upsampling prior to quantizing the estimated displacement.

15. The device of claim 1, where the cross-correlation algorithm applies a two-dimensional speckle tracking procedure.

16. The device of claim 1, wherein the cross-correlation coefficient comprises a complex function of axial lags and lateral lags.

17. The device of claim 1, wherein the one dimensional autocorrelation algorithm is applied in a slow time dimension corresponding to a tracking time.

18. The device of claim 1, wherein the cross-correlation algorithm is a two-dimensional cross-correlation algorithm.

19. The device of claim 1, wherein the motion tracking circuitry is further configured to estimate where a phase of said cross-correlation coefficient crosses zero.

20. The device of claim 1, said cross-correlation algorithm including cross-correlation over a search area that, subject to an image matching criterion, is incrementally increased.

21. The device of claim 1, further comprising multiple ultrasound imaging probes for respective imaging via said multiple acoustic windows.

22. An ultrasound motion-estimation method comprising:
issuing multiple ultrasound pulses, spaced apart from each other in a propagation direction of a shear wave, said shear wave having been induced by an axially-directed push;
tracking, with the multiple ultrasound pulses, axial motion caused by said shear wave;
based on said tracking of the axial motion, using autocorrelation to estimate an axial displacement and to quantize the estimate of axial displacement based on consecutive sampling depths to produce a quantized axial displacement; and
using the quantized axial displacement as a pixel-specific starting point in a time-domain based motion tracking algorithm including cross-correlation, wherein the using the quantized axial displacement as a pixel-specific starting point includes positioning a kernel for the cross-correlation by offsetting a kernel used in the autocorrelation by the quantized axial displacement, wherein the time-domain based motion tracking algorithm further includes:
using an axial lag associated with a maximum cross-correlation coefficient found by the cross-correlation in an interpolation to find a peak cross-correlation coefficient;
deriving a maximum axial lag from the peak cross-correlation coefficient; and
summing the maximum axial lag and the quantized axial displacement to derive a modified measurement of the axial displacement.

23. A non-transitory computer readable medium for ultrasound motion-estimation, said medium embodying a program having instructions executable by a processor for performing a plurality of acts, among said plurality there being the acts of:
issuing multiple ultrasound pulses, spaced apart from each other in a propagation direction of a shear wave, said shear wave having been induced by an axially-directed push;
tracking, with the multiple ultrasound pulses, axial motion caused by said shear wave;
based on said tracking of the axial motion, using autocorrelation to estimate an axial displacement and to quantize the estimate of axial displacement based on consecutive sampling depths to produce a quantized axial displacement;
using the quantized axial displacement to positioning a kernel for cross-correlation by offsetting a kernel used in the autocorrelation by the quantized axial displacement;
using an axial lag associated with a maximum cross-correlation coefficient found by the cross-correlation in an interpolation to find a peak cross-correlation coefficient;
deriving a maximum axial lag from the peak cross-correlation coefficient; and
summing the maximum axial lag and the quantized axial displacement to derive a modified measurement of the axial displacement.

* * * * *